(12) United States Patent
Begliomini et al.

(10) Patent No.: US 8,637,059 B2
(45) Date of Patent: Jan. 28, 2014

(54) FUNGICIDAL MIXTURES BASED ON CARBAMATE DERIVATIVES AND INSECTICIDES

(75) Inventors: Edson Begliomini, Sao Paulo (BR); Sergio Zambon, Piracicaba (BR)

(73) Assignee: BASF SE, Ludwigshafen (DE)

( * ) Notice: Subject to any disclaimer, the term of this patent is extended or adjusted under 35 U.S.C. 154(b) by 1972 days.

(21) Appl. No.: 10/583,003

(22) PCT Filed: Dec. 15, 2004

(86) PCT No.: PCT/EP2004/014277
§ 371 (c)(1),
(2), (4) Date: Jun. 13, 2006

(87) PCT Pub. No.: WO2005/058040
PCT Pub. Date: Jun. 30, 2005

(65) Prior Publication Data
US 2007/0093543 A1    Apr. 26, 2007

(30) Foreign Application Priority Data

Dec. 18, 2003  (EP) ..................... 03029169

(51) Int. Cl.
*A01N 25/08* (2006.01)
(52) U.S. Cl.
USPC ............ 424/405; 424/409; 514/404; 514/407
(58) Field of Classification Search
USPC ...................................................... 514/404
See application file for complete search history.

(56) References Cited

U.S. PATENT DOCUMENTS

| | | | |
|---|---|---|---|
| 5,747,516 A * | 5/1998 | Brown et al. ................. | 514/359 |
| 5,869,517 A | 2/1999 | Müller et al. | |
| 6,054,592 A | 4/2000 | Müller et al. | |
| 6,207,692 B1 | 3/2001 | Müller et al. | |
| 6,514,998 B1 | 2/2003 | Müller et al. | |

FOREIGN PATENT DOCUMENTS

| | | |
|---|---|---|
| EP | 0 295 117 A1 | 12/1988 |
| WO | WO 96/01256 | 1/1996 |
| WO | WO 96/01258 | 1/1996 |
| WO | WO99/48366 | 9/1999 |

* cited by examiner

*Primary Examiner* — Neil Levy
(74) *Attorney, Agent, or Firm* — Brinks Gilson & Lione

(57) ABSTRACT

The present invention relates to mixtures comprising as active components a) carbamate derivatives of the formula (I) in which the substituents and the index have the following meaning: T is CH or N n is 0, 1 or 2 R is halogen, $C_1$-$C_4$-alkyl or $C_1$-$C_4$-haloalkyl, it being possible for the radicals R to be different when n is 2, and b) at least one compound of the formula (II).

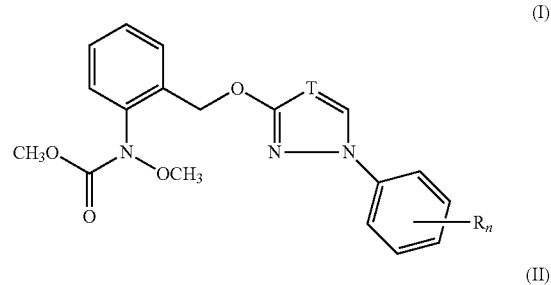

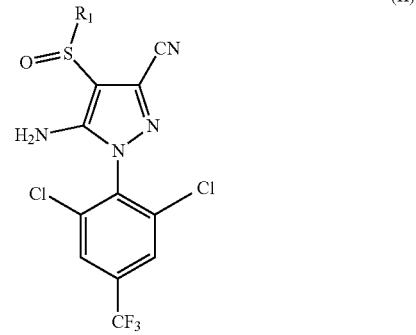

26 Claims, No Drawings

FUNGICIDAL MIXTURES BASED ON CARBAMATE DERIVATIVES AND INSECTICIDES

The present invention relates to mixtures comprising as active components a) carbamate derivatives of the formula I

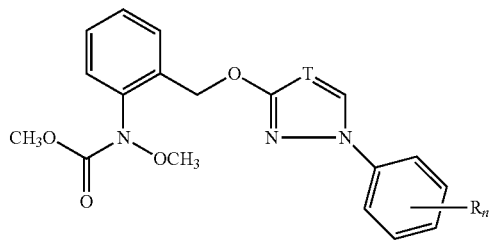

in which the substituents and the index have the following meaning:

T is CH or N n is 0, 1 or 2

R is halogen, $C_1$-$C_4$-alkyl or $C_1$-$C_4$-haloalkyl, it being possible for the radicals R to be different when n is 2, and b) at least one compound of the formula II

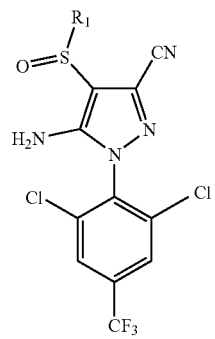

in which $R_1$ is $C_1$-$C_4$-alkyl or $C_1$-$C_4$-haloalkyl.

The combating of harmful phytopathogenic fungi is in many regions not the only problem the farmer has to face. Also harmful insects can cause a great damage to crops and other plants.

Thus, an efficient combination of fungicidal and insecticidal activity is desirable to overcome this problem.

Thus, it is an object of the present invention to provide a mixture which, on the one hand, has good fungicidal activity, and, on the other hand, good insecticidal activity, resulting in a broader pesticidal spectrum of action. More particularly, the subject of the present invention is a mixture for protecting plants against diseases and insects, characterized in that it comprises an effective amount of a fungicide and at least an effective amount of an insecticide. Furthermore it is an object of the present invention to provide a process for treating plants using these mixtures.

We have found that this object is achieved by a mixture comprising as active components a) carbamate derivatives of the formula I

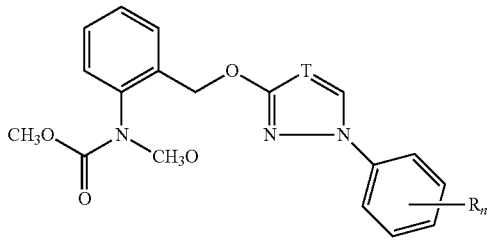

in which the substituents and the index have the following meaning:

T is CH or N n is 0, 1 or 2

R is halogen, $C_1$-$C_4$-alkyl or $C_1$-$C_4$-haloalkyl, it being possible for the radicals R to be different when n is 2, and b) at least one compound of the formula II

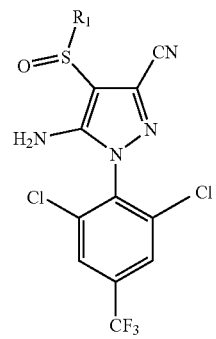

in which $R_1$ is $C_1$-$C_4$-alkyl or $C_1$-$C_4$-haloalkyl.

Furthermore we have found a process for treating plants using these mixtures.

The compounds of the formula I, their preparation and their action against harmful fungi have been disclosed in the literature (WO-A 96/01256 and WO-A 96/01258).

The compounds II, their preparation and their action against harmful insects has also been disclosed (EP 295 117).

Preferably, the compounds of formula I represent carbamate derivatives in which the combination of the substituents corresponds to one line of table 1 which follows:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |

TABLE 1-continued

| No. | T | $R_n$ |
|---|---|---|
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

More preferred are compounds I.12, I.23, I.32 and I.38, particularly preferred is compound I.32.

The compounds of formula II represent phenylpyrazoles, in which $R_1$ is $C_1$-$C_4$-alkyl or $C_1$-$C_4$-haloalkyl, preferably ethyl (common name: ethiprole) or trifluormethyl (common name: fipronil), more preferably trifluormethyl.

The compounds of formulae I and II are capable of forming salts or adducts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, lactic acid, succinic acid, citric acid, benzoic acid, cinnamic acid, oxalic acid, p-toluenesulfonic acid, salicylic acid, p-aminosalicylic acid, 2-phenoxybenzoic acid or 2-acetoxybenzoic acid.

Suitable metal ions are in particular the ions of the elements of the first to eighth transition group, especially chromium, manganese, iron, cobalt, nickel, copper, zinc, and additionally those of the second main group, especially calcium and magnesium, and of the third and fourth main group, in particular aluminum, tin and lead. If appropriate, the metals can be present in the different valencies that they can assume.

When preparing the mixtures, it is preferred to employ the substantially pure, especially the pure active compounds of formulae I and II, to which further active ingredients against harmful fungi or against other pests, such as insects or nematodes, can be added. Thus, a further active ingredient can be optionally added, for example at least one additional insecticide or fungicide, preferably an additional fungicide.

Preferred insecticides are those selected from the group consisting of organophosphates such as acephate, azinphos-methyl, chlorpyrifos, chlorfenvinphos, diazinon, dichlorvos, dicrotophos, dimethoate, disulfoton, ethion, fenitrothion, ffenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos, trichlorfon;

carbamates such as alanycarb, benfuracarb, carbaryl, carbosulfan, fenoxycarb, furathiocarb, indoxacarb, methiocarb, methomyl, oxamyl, Pirimicarb, Propoxur, Thiodicarb, Triazamate, Carbofuran;

pyrethroids such as Bifenthrin, Cyfluthrin, Cypermethrin, Deltamethrin, esfenvalerate, ethofenprox, fenpropathrin, fenvalerate, cyhalothrin, lambdacyhalothrin, permethrin, silafluofen, tau-fluvalinate, tefluthrin, tralomethrin, zetacypermethrin;

arthropod growth regulators such as a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide; c) juvenoids: pyriproxyfen, methoprene, fenoxycarb; d) lipid biosynthesis inhibitors: spirodiclofen;

various such as abamectin, acequinocyl, acetamiprid, amitraz, azadirachtin, bifenazate, cartap, chlorfenapyr, chlordimeform, cyromazine, diafenthiuron, dinetofuran, diofenolan, emamectin, endosulfan, fenazaquin, formetanate, formetanate hydrochloride, hydramethylnon, imidacloprid, indoxacarb, pyridaben, pymetrozine, spinosad, sulfur, tebufenpyrad, thiamethoxam, and thiocyclam.

Preferred fungicides are those selected from the group consisting of acylalanines such as benalaxyl, metalaxyl, ofurace, oxadixyl;

amine derivatives such as aldimorph, dodine, dodemorph, fenpropimorph, fenpropidin, guazatine, iminoctadine, spiroxamin, tridemorph;

anilinopyrimidines such as pyrimethanil, mepanipyrim or cyrodinyl;

antibiotics such as cycloheximid, griseofulvin, kasugamycin, natamycin, polyoxin or streptomycin;

azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

dicarboximides such as iprodion, myclozolin, procymidon, vinclozolin;

dithiocarbamates such as ferbam, nabam, maneb, mancozeb, metam, metiram, propineb, polycarbamate, thiram, ziram, zineb;

heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

copper fungicides such as Bordeaux mixture, copper acetate, copper oxychloride, basic copper sulfate;

nitrophenyl derivatives such as binapacryl, dinocap, dinobuton, nitrophthal-isopropyl;

phenylpyrroles such as fenpiclonil or fludioxonil;

sulfur other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid;

strobilurins such as azoxystrobin, dimoxystrobin, fluoxastrobin, kresoxim-methyl, metominostrobin, orysastrobin, picoxystrobin or trifloxystrobin;

sulfenic acid derivatives such as captafol, captan, dichlofluanid, folpet, tolylfluanid;

cinnemamides and analogs such as dimethomorph, flumetover or flumorph.

More preferred fungicides are those selected from the group consisting of acylalanines such as benalaxyl, metalaxyl, ofurace, oxadixyl;

azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

dicarboximides such as iprodion, myclozolin, procymidon, vinclozolin;

dithiocarbamates such as ferbam, nabam, maneb, mancozeb, metam, metiram, propineb, polycarbamate, thiram, ziram, zineb;

heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid;

strobilurins such as azoxystrobin, dimoxystrobin, fluoxastrobin, kresoxim-methyl, metominostrobin, orysastrobin, picoxystrobin or trifloxystrobin; sulfenic acid derivatives such as captafol, captan, dichlofluanid, folpet, tolylfluanid;

cinnemamides and analogs such as dimethomorph, flumetover or flumorph.

Especially preferred fungicides are those selected from metalaxyl;

bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

iprodione;

thiram;

benomyl, boscalid, carbendazin, carboxin, thiabendazole, thiophanate-methyl;

metrafenone, penycuron;

dimoxystrobin;

captan; and dimethomorph.

The most preferred fungicides are those selected from thiophanate-methyl, benomyl, carbendazim and thiabendazole.

In another preferred embodiment the most preferred fungicides are selected from metalaxyl, triticonazole, carbetazin, boscalid and thiophanate-methyl.

An extraordinary preferred fungicide is metalaxyl.

In another preferred embodiment the extraordinary preferred fungicide is triticonazole.

In another preferred embodiment the extraordinary preferred fungicide is carbetazin.

In another preferred embodiment the extraordinary preferred fungicide is boscalid.

In another preferred embodiment the extraordinary preferred fungicide is thiophanate-methyl.

In a preferred embodiment the mixture comprises the compound I.32 and fipronil.

In another preferred embodiment the mixture comprises the compound I.32 and ethiprole.

In a preferred embodiment the mixture comprises the compound I.32, fipronil and a further fungicide.

In another preferred embodiment the mixture comprises the compound I.32, fipronil and a further fungicide.

In another preferred embodiment the mixture comprises the compound I.32, fipronil and an acylalanine such as benalaxyl, metalaxyl, ofurace or oxadixyl, especially metalaxyl.

In another preferred embodiment the mixture comprises the compound I.32, fipronil and an azole such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole or flutriafol, especially tritoconazole.

In another preferred embodiment the mixture comprises the compound I.32, fipronil and a dicarboximide such as iprodione, myclozolin, procymidon or vinclozolin, especially iprodione.

In another preferred embodiment the mixture comprises the compound I.32, fipronil and a dithiocarbamate such as ferbam, nabam, maneb, mancozeb, metam, metiram, propineb, polycarbamate, thiram, ziram or zineb, especially thiram;

In another preferred embodiment the mixture comprises the compound I.32, fipronil and a heterocyclic compound such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole or triforine; especially benomyl, boscalid, carbendazin, carboxin, thiabendazole or thiophanate-methyl. In particular the mixture comprises the compound I.32, fipronil and boscalid. Also in particular the mixture comprises the compound I.32, fipronil and carbentazin. Also I in particular the mixture comprises the compound I.32, fipronil and thiophanate-methyl.

In another preferred embodiment the mixture comprises the compound I.32, fipronil and a further fungicide other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene or zoxamid, especially metrafenone or penycuron.

In another preferred embodiment the mixture comprises the compound I.32, fipronil and a strobilurin such as azoxystrobin, dimoxystrobin, fluoxastrobin, kresoxim-methyl, metominostrobin, orysastrobin, picoxystrobin or trifloxystrobin; especially dimoxystrobin.

In another preferred embodiment the mixture comprises the compound I.32, fipronil and a sulfenic acid derivative such as captafol, captan, dichlofluanid, folpet or tolylfluanid, especially captan.

In another preferred embodiment the mixture comprises the compound I.32, fipronil and a cinnemamide or ananalog thereof such as dimethomorph, flumetover or flumorph, especially dimethomorph.

In another preferred embodiment the mixture comprises two active ingredients only. The respective preferred embodiments are in accordance with the above-mentioned ones.

In another preferred embodiment the mixture comprises three active ingredients only. The respective preferred embodiments are in accordance with the above-mentioned ones.

In a preferred embodiment, the mixtures according to the invention are used for combating harmful fungi and harmful insects or nematodes.

In a further preferred embodiment, the mixtures according to the invention are used for combating harmful fungi.

In a further preferred embodiment, the mixtures according to the invention are used for combating harmful insects or nematodes.

In a further particular preferred embodiment, the mixtures according to the invention comprise the compounds of formula I and formula II in a synergistic effective amount and are used for combating harmful fungi.

In a further particular preferred embodiment, the mixtures according to the invention comprise the compounds of formula I and formula II in a synergistic effective amount and are used for combating harmful insects or nematodes.

The mixtures according to the invention are especially important for controlling a large number of fungi and insects or nematodes on a variety of crop plants such as wheat, corn, rye, barley, oats, sorghum, rice, maize, grass, bananas, cotton, soy beans, coffee, sugar cane, grapevines, fruit species, omamentals and vegetables such as cucumbers, beans, drybeans, tomatoes, potatoes, lettuce, cucurbits, cabbage, carrots, cruciferous, sunflowers and cucurbits, and on the seeds of these plants or on pasture and on seeds of pasture. In a special embodiment the mixtures according to the present invention are applied on soybeans. In another preferred embodiment the mixtures according the present invention are applied on seeds. In a particular embodiment the mixtures according to the present invention are applied on seeds of soybeans.

Specifically, they are suitable for controlling the following harmful fungi:

Alternaria species on vegetables and fruit,
Bipolaris and Drechslera species on cereals, rice and turf,
Blumeria graminis (powdery mildew) on cereals,
Botrytis cinerea (gray mold) on strawberries, vegetables, ornamentals and grapevines,
Erysiphe cichoracearum and Sphaerotheca fuliginea on cucurbits,
Fusarium and Verticillium species on various plants,
Mycosphaerella species on cereals, bananas and peanuts,
Phakopsara pachyrhizi and Phakopsara meibomiae on soybeans
Phytophthora infestans on potatoes and tomatoes,
Plasmopara viticola on grapevines,
Podosphaera leucotricha on apples,
Pseudocercosporella herpotrichoides on wheat and barley,
Pseudoperonospora species on hops and cucumbers,
Puccinia species on cereals,
Pyricularia oryzae on rice,
Rhizoctonia species on cotton, rice and turf,
Septoria tritici and Stagonospora nodorum on wheat,
Uncinula necator on grapevines,
Ustilago species on cereals and sugar cane, and
Venturia species (scab) on apples and pears.

They are also suitable for controlling the following harmful insects from the order of the lepidopterans (Lepidoptera), for example Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feftia subterranea, Galleria mellonella, Grapholitha funebrana, Grapholitha molesta, Heliothis armigera, Heliothis virescens, Heliothis zea, Hellula undalis, Hibemia defoliaria, Hyphantria cunea, Hyponomeuta malinelus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomana linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi,

*Diabrotica longicomis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius califomicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria*, dipterans (Diptera), for example *Aedes aegypti, Aedes vexans, Anastrepha ludens, Anopheles maculipennis, Qeratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (Thysanoptera), e.g. *Frankliniella fusca, Frankliniella occidentalis, Frankliniella tritici, Scirtothrips citri, Thrips oryzae, Thrips palmi* and *Thrips tabaci*, hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta*, heteropterans (Heteroptera), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, homopterans (Homoptera), e.g. *Acyrthosiphon onobrychis, Adelges laricis, Aphidula nasturtil, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardul, Brachycaudus helichrysi, Brachycaudus persicae, Brachycaudus prunicola, Brevicoryne brassicae, Capitophorus homi, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolli*.

termites (Isoptera), e.g. *Calotennes flavicollis, Leucotermes flavipes, Reticulitermes lucifugus* and *Termes natalensis*, orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentorsilvarum, Hyalomma truncatum, Ixodes ricinus, Ixodes rubicundus, Omithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;*

They are furthermore suitable for controlling the following harmful nematodes, especially plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifoli,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formulae I and II and optionally the further active ingredient(s) can be applied simultaneously, that is jointly or separately, or in succession; the sequence, in the case of separate application, generally not having any effect on the result of the control measures.

The compounds of formulae I and II are usually applied in an effective amount, preferably in a weight ratio of from 100:1 to 1:100, in particular from 20:1 to 1:20, preferably from 10:1 to 1:10.

The compounds of formula I and the further fungicide are usually applied in an effective amount, preferably in a weight ratio of from 1000:1 to 1:1000.

Depending on the desired effect, the application rates of the mixtures according to the invention are, especially in the case of areas under agricultural cultivation, from 5 to 2 000 g/ha, preferably from 50 to 1 500 g/ha, in particular from 50 to 750 g/ha.

Here, the application rates of the compounds of formula I are from 1 g to 1 kg/ha, preferably from 10 to 900 g/ha, in particular from 20 to 750 g/ha.

Correspondingly, the application rates of the compounds of formula II are from 1 g to 1 kg/ha, preferably from 10 to 750 g/ha, in particular from 20 to 500 g/ha.

Correspondingly, the application rates of the further fungicide are from 1 g to 1 kg/ha, preferably from 5 to 900 g/ha, in particular from 10 to 750 g/ha.

In the treatment of seed, the application rates of the mixture according to the invention are generally from 0.1 to 1 000 g/100 kg of seed, preferably from 0.1 to 200 g/100 kg, in particular from 1 to 100 g/100 kg.

A further embodiment of the present invention is directed to the seeds being treated with the mixture according to the present invention.

In the control of phytopathogenic harmful fungi and/or harmful insects and/or nematodes, especially in the control of phytopathogenic harmful fungi and/or harmful insects, the separate or joint application of the compounds of formulae I and II and optionally of the further active ingredient or of a mixture according to the invention is carried out by treating the seeds, the plants or the soils before or after sowing of the plants or before or after emergence of the plants.

The mixtures according to the invention can be prepared, for example, in the form of directly sprayable solutions, powders and suspensions or in the form of highly concentrated aqueous, oily or other suspensions, dispersions, emulsions, oil dispersions, pastes, dusts, compositions for spreading or granules, and be applied by spraying, atomizing, dusting, broadcasting or watering or colored suspension, solution, emulsion to be applied as such or as water based slurry with seed treatment machinery. The use form depends on the particular purpose; in each case, it should ensure a distribution of the mixture according to the invention, which is as fine and uniform as possible.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), DMSO, acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignin-sulfte waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose and ethyleneoxide/propyleneoxide block copolymers.

For seed treatment, also regulators such as *Azosprillium* species and *Bradyrhizobium* species such as *Bradyrhizobium japonicum* can be added to the mixtures according to the present invention.

For seed treatment, also pigments can be added. Suitable pigments for seed treatment are pigment blue 15:3, pigment yellow 1, pigment red 112, pigment red 48:2, pigment red 57:1, Pigment red 53:1, pigment orange 43, pigment orange 5, pigment green 36, pigment green 7, pigment white 6.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate; magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations:
1. Products for Dilution with Water
A) Water-soluble Concentrates (SL, LS)

10 parts by weight of the active compounds are dissolved in water or in a water-soluble solvent. As an alternative, wetters or other auxiliaries are added. The active compound dissolves upon dilution with water.

B) Dispersible Concentrates (DC)

20 parts by weight of the active compounds are dissolved in cyclohexanone with addition of a dispersant, for example polyvinylpyrrolidone. Dilution with water gives a dispersion.

C) Emulsifiable Concentrates (EC)

15 parts by weight of the active compounds are dissolved in xylene with addition of calcium dodecylbenzenesulfonate and castor oil ethoxylate (in each case 5% strength). Dilution with water gives an emulsion.

D) Emulsions (EW, EO, ES)

40 parts by weight of the active compounds are dissolved in xylene with addition of calcium dodecylbenzenesulfonate and castor oil ethoxylate (in each case 5% strength). This mixture is introduced into water by means of an emulsifier machine (Ultraturvax) and made into a homogeneous emulsion. Dilution with water gives an emulsion.

E) Suspensions (SC, OD, FS)

In an agitated ball mill, 20 parts by weight of the active compounds are comminuted with addition of dispersant, wetters and water or an organic solvent to give a fine active compound suspension. Dilution with water gives a stable suspension of the active compound.

F) Water-dispersible Granules and Water-soluble Granules (WG, SG)

50 parts by weight of the active compounds are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-dispersible Powders and Water-soluble Powders (WP, SP, WS)

75 parts by weight of the active compounds are ground in a rotor-stator mill with addition of dispersant, wetters and silica gel. Dilution in water gives a stable dispersion or solution with the active compound.

2. Products to be Applied Undiluted
H) Dustable Powders (DP, DS)

5 parts by weight of the active compounds are ground finely and mixed intimately with 95% of finely divided kaolin. This gives a dustable product.

I) Granules (GR, FG, GG, MG)

0.5 parts by weight of the active compounds is ground finely and associated with 95.5% carriers. Current methods are extrusion, spray-drying or the fluidized bed. This gives granules to be applied undiluted.

J) ULV Solutions (UL)

10 parts by weight of the active compounds are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate just immediately prior to use (tank mix). These agents can be admixed with the agents according to the invention in a weight ratio of 1:10 to 10:1.

The mixtures according to the invention or the corresponding formulations comprising a mixture according to the invention are applied by treating the harmful fungi, their habitat or the plants, seeds, soils, areas, materials or spaces to be kept free from them and the insects or nematodes or their food supply, habitat or breeding grounds with a fungicidally and insecticidally effective amount of the mixture according to the invention or, in the case of separate application, of the compounds of formulae I and II and optionally at least a further active ingredient.

The mixtures according to the invention or the corresponding formulations comprising a mixture according to the invention are applied by treating the harmful fungi, their habitat or the plants, seeds, soils, areas, materials or spaces to be kept free from them with a fungicidally effective amount of the mixture according to the invention or, in the case of separate application, of the compounds of formulae I and II and optionally at least a further active ingredient.

The mixtures according to the invention or the corresponding formulations comprising a mixture according to the invention are applied by treating the insects or nematode or their food supply, habitat or breeding grounds with a insecticidally effective amount of the mixture according to the invention or, in the case of separate application, of the compounds of formulae I and II and optionally at least a further active ingredient.

The testing of the mixtures according to the present invention shows that said mixtures are effective in controlling fungi and/or insects and/or nematodes.

We claim:

1. A mixture for crop protection, comprising as active components
a) carbamate derivatives of the formula I

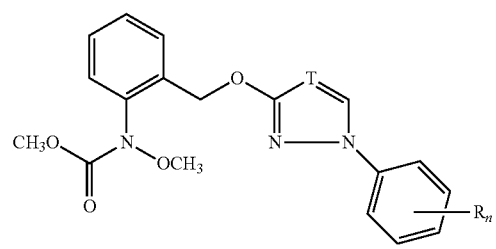

in which the substituents and the index have the following meaning:

T is CH or N;

n is 0, 1 or 2; and each R is independently halogen, $C_1$-$C_4$-alkyl or $C_1$-$C_4$-haloalkyl, it being possible for the radicals R to be different when n is 2, and b) at least one compound of the formulae II in which $R_1$ is $C_1$-$C_4$-alkyl or $C_1$-$C_4$-haloalkyl.

2. A mixture as claimed in claim 1, wherein $R_1$ is trifluoromethyl.

3. A mixture as claimed in claim 1, wherein $R_1$ is ethyl.

4. A mixture as claimed in claim 1, further comprising a fungicide.

5. A mixture as claimed in claim 4, wherein the fungicide is metalaxyl, triticonazole, carbetazin, boscalid or thiophanate-methyl.

6. A mixture as claimed in claim 1, wherein the weight ratio of the compound of formula I to compound of formula II is from 100:1 to 1:100.

7. A mixture as claimed in claim 4, wherein the weight ratio of the compounds of formula I to the fungicide is from 1000:1 to 1:1000.

8. A composition comprising a solid or liquid carrier and a mixture comprising:

a) carbamate derivatives of the formula I in which the substituents and the index have the following meaning:

T is CH or N;

n is 0, 1 or 2; and each R is independently halogen, $C_1$-$C_4$-alkyl or $C_1$-$C_4$-haloalkyl, it being possible for the radicals R to be different when n is 2, and b) at least one compound of the formulae II in which $R_1$ is $C_1$-$C_4$-alkyl or $C_1$-$C_4$-haloalkyl.

9. A method for controlling phytopathogenic harmful fungi, which comprises treating the harmful fungi, their habitat or the plants, seeds, soils, areas, materials or spaces to be kept free from them with a mixture as set forth in claim 1.

10. The method as claimed in claim 9, wherein the mixture is applied in an amount of from 5 g/ha to 2,000 g/ha.

11. The method as claimed in claim 9, wherein the mixture is applied in an amount of from 1 to 1,000 g/100 kg of seed.

12. A method for controlling harmful insects, which comprises treating an insect, arachnid or nematode or their food supply, habitat or breeding grounds with a mixture as set forth in claim 1.

13. The method as claimed in claim 12, wherein the mixture is applied in an amount of from 5 g/ha to 2,000 g/ha.

14. The method as claimed in claim 12, wherein the mixture is applied in an amount of from 1 to 1,000 g/100 kg of seed.

15. A method for controlling phytopathogenic harmful fungi and harmful insects, which comprises treating the harmful fungi, their habitat or the plants, seeds, soils, areas, materials or spaces to be kept free from them or the insect or nematode or their food supply, habitat or breeding grounds with a mixture as set forth in claim 1.

16. The method as claimed in claim 15, wherein the mixture is applied in an amount of from 5 g/ha to 2,000 g/ha.

17. The method as claimed in claim 15, wherein the mixture is applied in an amount of from 1 to 1,000 g/100 kg of seed.

18. A method for controlling phytopathogenic harmful fungi, which comprises treating the harmful fungi, their habitat or the plants, seeds, soils, areas, materials or spaces to be kept free from them with a composition as set forth in claim 8.

19. The method as claimed in claim 18, wherein the composition is applied in an amount of from 5 g/ha to 2,000 g/ha.

20. The method as claimed in claim 18, wherein the composition is applied in an amount of from 1 to 1,000 g/100 kg of seed.

21. A method for controlling harmful insects, which comprises treating an insect, arachnid or nematode or their food supply, habitat or breeding grounds with a composition as set forth in claim 8.

22. The method as claimed in claim 21, wherein the composition is applied in an amount of from 5 g/ha to 2,000 g/ha.

23. The method as claimed in claim 21, wherein the composition is applied in an amount of from 1 to 1,000 g/100 kg of seed.

24. A method for controlling phytopathogenic harmful fungi and harmful insects, which comprises treating the harmful fungi, their habitat or the plants, seeds, soils, areas, materials or spaces to be kept free from them or the insect or nematode or their food supply, habitat or breeding grounds with a composition as set forth in claim 8.

25. The method as claimed in claim 24, wherein the composition is applied in an amount of from 5 g/ha to 2,000 g/ha.

26. The method as claimed in claim 24, wherein the composition is applied in an amount of from 1 to 1,000 g/100 kg of seed.

* * * * *